(12) United States Patent
Koshti et al.

(10) Patent No.: US 6,613,340 B2
(45) Date of Patent: Sep. 2, 2003

(54) SUBSTANTIVE HYDROPHOBIC CATIONIC UV-ABSORBING COMPOUNDS

(75) Inventors: Nirmal Madhukar Koshti, Maharashtra (IN); Arun Harchandra Jawale, Maharashtra (IN); Bharat Bhikaji Parab, Maharashtra (IN); Shubhangi Dattaram Naik, Maharashtra (IN); Manasi Dattatraya Moghe, Maharashtra (IN); Tanaji Shamrao Jadhav, Maharashtra (IN); Subhash Shivling Nashte, Maharashtra (IN)

(73) Assignee: Galaxy Surfactants Ltd., Maharashtra (IN)

( * ) Notice: Subject to any disclaimer, the term of this patent is extended or adjusted under 35 U.S.C. 154(b) by 0 days.

(21) Appl. No.: 09/917,726

(22) Filed: Jul. 31, 2001

(65) Prior Publication Data

US 2003/0064083 A1 Apr. 3, 2003

(30) Foreign Application Priority Data

Jan. 23, 2001 (IN) .................................................. 77/01
Feb. 23, 2001 (IN) ............................................. 196/2001

(51) Int. Cl.$^7$ ............................ A61K 7/42; A61K 7/00; A61K 7/06
(52) U.S. Cl. ...................... 424/401; 424/59; 424/90.1; 424/400; 514/617; 514/619; 514/643; 564/133; 564/134; 564/139; 564/169; 564/166; 564/170; 564/182; 564/284; 564/287; 564/288
(58) Field of Search ................................. 514/617, 619, 514/643; 564/133, 134, 139, 164, 166, 170, 182, 284, 287, 288; 424/401, 59, 70.1, 400

(56) References Cited

FOREIGN PATENT DOCUMENTS

EP   0 165 710   * 12/1985   ......... C07C/101/62

OTHER PUBLICATIONS

Database CAPLUS on STN, Acc. No. 1986:502334, Saettone et al., 'Substantivity of sunscreens: and appraisal of some quaternary ammonium sunscreens.' Int. J. Cosmet. Sci. (1986), 8(1), pp. 9–25 (abstract).*

* cited by examiner

Primary Examiner—Brian Davis
(74) Attorney, Agent, or Firm—Birch, Stewart, Kolasch & Birch, LLP

(57) ABSTRACT

Substantive UV absorbing organic-soluble quaternary salts of cinnamidoalkylamine are described. Hair, skin and fabric care compositions containing the compounds of formula I.

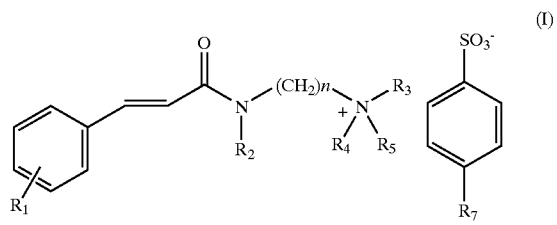

wherein $R_1$ is a substituent, selected from H, halo, —OH, —NH$_2$, —NO$_2$, —OCH$_3$, —N(CH$_3$)$_2$, alkyl groups containing from 1 to 6 carbon atoms, alkoxy groups containing from 1 to 6 carbon atoms, alkylamino or N,N-dialkylamino groups containing from 1 to 6 carbon atoms; $R_2$ is selected from hydrogen, alkyl group containing from 1 to 12 carbon atoms; $R_3$ and $R_4$ are independently selected from benzyl, alkyl group containing from 1 to 12 carbon atoms; n is an integer from 1 to 6; $R_5$ is selected from an alkyl group containing from 8 to 22 carbon atoms; alkenyl groups containing from 8 to 22 carbon atoms; $R_7$ is selected from bromo, chloro, nitro, methyl and ethyl groups.

16 Claims, No Drawings

SUBSTANTIVE HYDROPHOBIC CATIONIC UV-ABSORBING COMPOUNDS

FIELD OF INVENTION

The invention relates to substantive hydrophobic cationic UV-absorbing compounds. More particularly, the invention relates to novel, cationic, non-hydrolysable, non-irritating UV-absorbing bis-quaternary salts of cinnamidoalkylamines which are substantive to fabric, skin and hair. The invention also relates to a process of manufacture of the said compounds and further to their use in hair, skin and fabric care formulations.

BACKGROUND AND PRIOR ART

The harmful effects of solar UV-radiation on skin are well known. The UV-B (290–320 nm) portion of solar spectrum is largely responsible for erythema (sunburn) and cancer. [M. M. Rieger, Cosmet. Toiletries, 102 (3), 91, (1987); L. Taylor, Skin Cancer Foundation J., 4, (90) (1986)].

Similarly, photodegradative effect of UV-radiation on human hair is well documented. Continuous exposure to sunrays lightens hair color and makes human hair rough, brittle and difficult to comb. UV rays are reported to damage the proteins of cuticles. Prolonged irradiation results in diminished tensile strength due to breaking of disulphide bonds in keratin. [R. Beyak et al, J. Soc. Cosmet. Chem. 22, 667–668 (1971), E. Hoting et al, J. Soc. Cosmet. Chem. 46, 85–99 (1995)].

In addition, UV light is also known to fade colored garments. [P. C. Screws, Text. Chem. Color, 11, 21 (1987); B. Milligan et al, Polym. Degrad. Stab. 10 (4), 335 (1985)].

A number of UV-absorbing compounds like derivatives of salicylic acid, benzophenones, benzotriazoles, cinnamic acid have been used in personal care products. However, all these molecules suffered from a major disadvantage of lack of substantivity. To make this UV-absorbing moieties more substantive, structural modification have been introduced. U.S. Pat. No. 5,427,773 (1995) discloses cationic substantive photofilters based on dimethylamino benzamide whereas U.S. Pat. No. 5,601,811 (1997) describes about cationic photofilters based on cinnamidoalkyl moiety for UV absorption that are water-soluble. High water-solubility is not always desirable for skin care applications due to possible toxic effects associated with long term usage of cosmetics on human skin. In terms of substantivity to the substrates like skin and hair, water-insoluble cationic photofilters were found to have superior substantivity when compared with water-soluble photofilters in rinse-off products.

The main object of the present invention is therefore to synthesise hydrophobic molecules containing most popular cinnamido moiety to provide UV-B absorption and with cationic centre to provide substantivity to skin, hair and fabric and a long alkyl chain to impart conditioning effect.

SUMMARY OF THE INVENTION

Thus the present invention provides a novel, substantive, organic-soluble cinnamidoalkylamine quaternary compounds of Formula I,

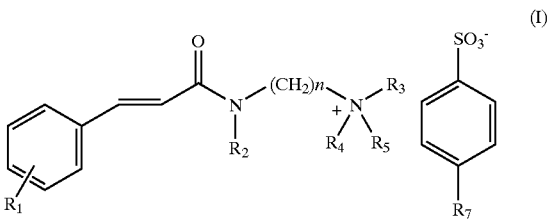

wherein $R_1$ is selected from H, halo, —OH, —NH$_2$, —NO$_2$, —OCH$_3$, —N(CH$_3$)$_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6;

$R_5$ is selected from an alkyl group containing from 8 to 22 carbon atoms; alkenyl groups containing from 8 to 22 carbon atoms;

$R_7$ is selected from bromo, chloro, nitro, methyl and ethyl groups.

A preferred compound of Formula I is, p-methoxy cinnamidopropyl dimethyllauryl ammonium tosylate, wherein, $R_1$=—OCH$_3$; $R_2$=—H; $R_3$,$R_4$=CH$_3$; n=3; $R_5$=—$C_{12}H_{25}$; $R_7$=—CH$_3$ is described.

In another aspect the invention relates to a process of making a quaternary ammonium salt of cinnamidoalkylamine Formula I,

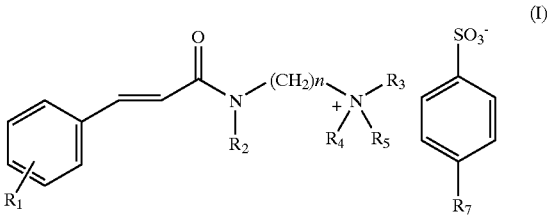

wherein $R_1$ is a substituent, selected from H, halo, —OH, —NH$_2$, —NO$_2$, —OCH$_3$, —N(CH$_3$)$_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen, alkyl group containing from 1 to 12 carbon atoms;

$R_3$ and $R_4$ are independently selected from benzyl, alkyl group containing from 1 to 12 carbon atoms, n is an integer from 1 to 6;

$R_5$ is selected from an alkyl group containing from 8 to 22 carbon atoms; alkenyl groups containing from 8 to 22 carbon atoms;

$R_7$ is selected from bromo, chloro, nitro, methyl and ethyl groups, wherein the process a compound of Formula II is reacted with a compound of Formula III to give an intermediate of Formula IV, the intermediate of formula IV is quaternised with a compound of Formula V, wherein, $R_1$, $R_2$, $R_3$, $R_4$, $R_5$, $R_7$, n are same as in Formula I and $R_6$ of Formula II is selected form —OH, Cl⁻ or —O(CH$_2$)$_p$CH$_3$ with p=0 to 3 to provide the compound of formula I.

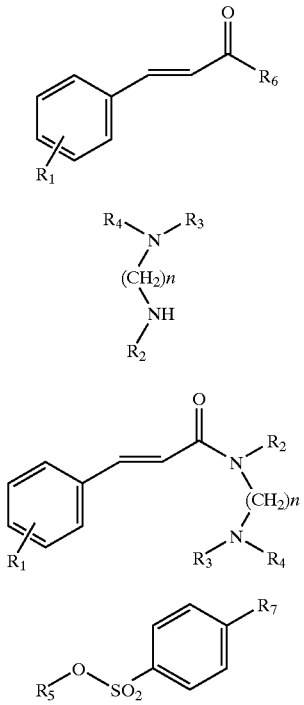

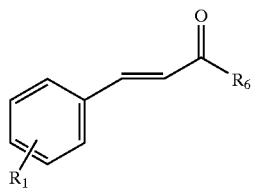

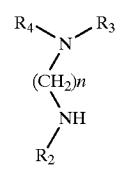

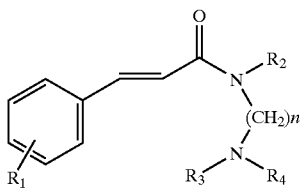

According to a further aspect of the present invention there is provided skin care, hair care and fabric care formulations containing novel organic-soluble cinnamidoalkylamine quaternary ammonium compounds of Formula I and conventional active ingredients of skin and hair care products.

The unique combination of substantivity to hair and skin, conditioning, strong UV absorption and water-insolubility of these quaternary compounds of cinnamidoalkylamines is very desirable for personal care products, especially for skin care applications.

DETAILED DESCRIPTION OF THE INVENTION

The substantive UV absorbing compounds of the present invention are quaternary salts of cinnamidoalkylamines that are prepared by reacting lower alkyl ester of cinnamic acid or acid halides of cinnamic acid with an amino compound that is subsequently quaternised with substituted benzene sulphonate esters of fatty alcohols. The preferred compounds of the present invention are water-insoluble quaternaries of cinnamidoalkylamines.

In the process, the amidification reaction between a compound of the Formula II when $R_6$=—OH or —O(CH$_2$)$_p$CH$_3$ with p=0 to 3, with that of Formula III is carried out at from about 120° C. to about 200° C., under pressure from about 10 psi to about 100 psi, in the presence of a basic catalyst such as sodium methoxide, sodium hydroxide from 0.25% to 5.0% by weight of the reaction mass, to afford the intermediate compound of Formula IV.

Preferred amount of such catalyst is 1.0% w/w of total reaction mass. The reaction is conveniently monitored by TLC or HPLC using UV detection. After the complete disappearance of cinnamic acid ester, the excess diamine is distilled off under vacuum.

Alternately, this reaction is carried out in the presence of a basic catalyst such as sodium methoxide, sodium hydroxide from 0.25% to 5.0% by weight of the reaction mass under atmospheric pressure, under blanket of nitrogen, with an arrangement for continuous selective removal of lower alcohol formed in the reaction.

Thus, the condensation reaction of one mole of cinnamic acid ester is carried with 1.0 to 3.0 moles of diamine at 120 to 200° C., preferably at 180° C., for 12 to 36 hours. The amines themselves can catalyse the reaction, however, the rates are found to be slower as compared with the bases like sodium methoxide and the like.

The same reaction can be performed using cinnamic acid in place of cinnamic acid ester at temperatures up to 200° C. and pressures of 100 psi, keeping the same stoichiometry (1:1.0 to 3). The excess diamine serves as solvent for the reaction.

Cinnamic acid esters and amino compounds are selected that are liquid within the disclosed temperature and pressure range. This reaction generates lower alcohol that need not be distilled out.

The amidification reaction between a compound of Formula II when $R_6$=—Cl in the presence of a solvent, is carried out with that of Formula III at room temperature in the presence of solvent. The compounds of Formula IV are synthesised by reacting acid chlorides of Formula II (1.0 mole) when $R_6$ is —Cl with the diamines of Formula III (1.0 to 1.2 mole) at 20–50° C. in an inert solvent like dichloromethane, ethylene dichloride, tetrahydrofuran and the like.

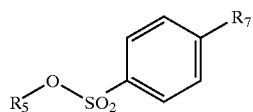

The alkylating agents used in the present invention are fatty alcohol esters of substituted benzene sulphonic acids of Formula V, wherein, $R_5$ and $R_7$ are same as in Formula I. Compounds of Formula V are synthesised from fatty alcohols, either pure or a mixture, by reacting with benzene sulphonyl chloride or tosyl chloride and the like in the presence of a suitable base. This esterification is carried out in aprotic solvents like tetrahydrofuran, dichloromethane. Fatty alcohols used in the present invention are of natural origin (vegetable oils) and synthetic origin (Ziegler, Oxo process). Thus, they are both branched or straight chain alcohols, n-octanol, n-dodecanol and the like. The long chain alcohols with a degree of unsaturation like oleyl alcohol are also suitable for the present invention.

Quaternization of cinnamidoamines is carried out in solvents that include, dimethyl formamide, tetrahydrofuran, lower branched alkanols such as isopropanol, t-butanol and combinations thereof. Mixtures of these solvents can also be used. Solvents used are from 20 to 80% by weight of the reaction mass. The cinnamidoalkylamines (Formula IV, 1 mole) are N-alkylated with quaternising agents (Formula V, 1.0 mole) in the presence of suitable solvents preferably such as THF, isopropanol that govern temperatures at which the reaction is carried out.

The quaternisation reaction can be conveniently done in a pressure reactor as well as in an open system. The temperatures suitable for pressure reaction range from about 60–125° C. with the pressures up to 50 psi. The pressures are governed by the amount of solvent and the temperature selected for the reaction. The conditions of reaction in an open vessel also get dictated by the choice of solvent. The reactions are usually carried out at boiling point or slightly below boiling point of the solvent employed. The resulting quaternary salts are obtained as concentrated solutions. The progress of the reaction is monitored by measuring the amount of unreacted alkylating agent by chromatography or by estimation of unquaternized amidoamine or by determining the active matter (the quaternised product) by two phase titration with anionic surfactant.

On Quaternization, the solvents are removed from concentrated solutions of quaternary ammonium salts to obtain solvent free pure compounds in the form of low melting solids.

Alternately, quaternisations can be carried out by directly reacting equimolar quantities of cinnamidoalkylamines of Formula IV with fatty alcohol esters of substituted benzene sulphonic acids of Formula V at from about 100 to 140° C. for 4 to 24 hours without any solvent and in an inert atmosphere of nitrogen.

In these cationic compounds as shown in Formula I, the benzene ring of cinnamidoalkylamine contains a substituent ($R_1$), preferably in para position and is selected from moieties such as —halo, —OH, —$NH_2$, —$NO_2$, —$OCH_3$, —$N(CH_3)_2$.

Referring again to Formula I, the amido nitrogen is preferably either unsubstituted ($R_2$ is hydrogen) or may contain a substituent, depicted in Formula I when $R_2$ is selected from alkyl groups containing from 1 to 12 carbon atoms.

The quaternized nitrogen of compounds in accordance with the present invention contains substituents, $R_3$ and $R_4$ as depicted in Formula I, same or different, preferably selected from benzyl and/or alkyl groups containing from 1 to 12 carbon atoms.

The compounds of the present invention are cationic photofilters containing cinnamidoalkylamines moiety as shown in Formula I, in which n is an integer between 1 and 6, both inclusive. Preferred cationic photofilters in accordance with the present invention are compounds containing cinnamidoalkylamines in which n is 3.

The compounds of the present invention are cationic quaternary ammonium salts having cinnamidoalkylamines as shown in Formula I, in which the quaternary nitrogen bears the fourth group $R_5$ that can be a fatty alkyl group containing from 8 to 22 carbons, both inclusive, and the alkyl chain can have unsaturation or branching.

Thus, the cationic photofilters of the present invention are formed by quaternising compounds of Formula IV by fatty alcohol esters of substituted benzene sulphonic acids of Formula V. The cationic photofilters of the present invention, also include an anion derived from quaternisation reactions. Given the quaternizing agents described above, the cationic compounds of the present invention will contain an anion, benzene sulphonate of Formula I, wherein, $R_7$ is selected from bromo, chloro, nitro and methyl groups.

Another embodiment of the present invention relates to manufacture of a compound of Formula I, in which $R_1$=para —$OCH_3$, $R_2$=—H, $R_3$=$R_4$=—$CH_3$, $R_5$=—$C1_{12}H_{25}$ to —$C_{18}H_{37}$, $R_7$=—$CH_3$, counter anion=tosylate anion and n=3, from the compounds of Formula II (p-methoxy ethyl cinnamate, $R_1$=—$OCH_3$, $R_6$=—$OC_2H_5$), Formula III (N,N-dimethylpropyldiamine, $R_2$=—H, $R_3$=$R_4$=—$CH_3$, n=3) forming an intermediate compound of Formula IV (p-methoxy cinnamidopropyldimethyl amine, $R_1$=—$OCH_3$, $R_2$=—H, $R_3$ and $R_4$=—$CH_3$) and Formula V (alkyl tosylate, $R_5$=—$C_{12}H_{25}$ to —$C_{18}H_{37}$, $R_7$=—$CH_3$). The process of preparation of one such compound of Formula I is given in Example I.

Another embodiment of the present invention relates to manufacture of a compound of Formula I, in which $R_1$=para —$OCH_3$, $R_2$=—H, $R_3$=$R_4$=—$CH_3$, $R_5$=—$C_{12}H_{25}$ to —$C_{18}H_{37}$, $R_7$=—$CH_3$, counter anion=tosylate anion and n=3, from the compounds of Formula II (p-methoxy cinnamoyl chloride, $R_1$=$OCH_3$, $R_6$=Cl), Formula III (N,N-dimethylpropyldiamine, $R_2$=—H, $R_3$=$R_4$=—$CH_3$, n=3) forming an intermediate compound of Formula IV (p-methoxy cinnamidopropyldimethyl amine, $R_1$=—$OCH_3$, $R_2$=—H, $R_3$ and $R_4$=—$CH_3$) and Formula V (alkyl tosylate, $R_5$=—$C_{12}H_{25}$ to —$C_{18}H_{37}$, $R_7$=—$CH_3$). The process of preparation of one such compound of Formula I is given in Example II.

The compounds of Formula I with substituents given in above two paragraphs are soluble in alcohols, glycols, mixtures thereof, mixtures of alcohols and water and mixtures of glycols and water. However, they are practically insoluble in water alone. Other suitable solvents can be polyethoxylated triglycerides, polyethoxylated fatty alcohols or ethoxylated silicones. These compounds are white to pale yellow solids with faint fatty odour. The substantive UV-B absorbers of the present invention are non-hydrolysable, non-irritant, non-mutagenic and compatible with commonly used cosmetic ingredients.

This invention provides compositions containing quaternary ammonium compounds of Formula I that are organic-soluble, UV-absorbing, conditioning and substantive to skin, hair and textile fibres. The hair care and skin care compositions containing compounds of Formula I can be solutions, dispersions or emulsions.

Lotions may be formed using compounds of Formula I, with or without one or more of the inert solvents like ethyl alcohol, isopropyl alcohol or propylene glycol, by combining with film forming polymers like proteins, polyvinyl pyrrolidone, polyvinyl alcohols and the like, film-forming starches and resins and the like.

Oil-in-water and water-in-oil emulsion can also be employed as vehicles for these compounds of Formula I to form lotions and creams. Conventional oil soluble UV-absorbing compounds like cinnamates, salicylates, p-aminobenzoates, benzophenones can be dissolved in oily phase of emulsion/lotions. The water-soluble sunscreens are dissolved in an aqueous phase of the emulsion and combined with the oily phase using a suitable cationic emulsifier such as stearylkonium chloride. Vegetable or mineral oils suitable for use as oil phase include mineral oil, petroleum, castor oil, sesame oil and the like. The quaternary ammonium compounds of the present invention are added to oily phase which is then subsequently emulsified with aqueous phase using an emulsifier like stearylkonium chloride or non-ionic emulsifiers like polysorbate-80, fatty alcohol ethoxylates and the like.

A preparation of cream hair conditioner of emulsion type having sunscreens of both the types, organic-soluble compounds of Formula I and water-soluble (organic-insoluble) sunscreens of our co-pending patent application (Indian Patent Appl. No. 903/Mum/2000 dated Oct. 6, 2000) is given in Example IV.

Perfumes, fragrances, anti-oxidants, preservatives, dyes colorants, insect repellents, fillers and suspended particulate matter, emollients, humectants, thickeners and the like may optionally be included in the sunscreen and tanning compositions of the present invention.

The sunscreen and tanning compositions of the present invention contain an effective amount of compounds of Formula I to prevent erythema. In general, an amount of about 0.5% to 10% w/w of the total composition is used.

For everyday use a sunscreen cream to protect the skin from both UV-A and UV-B radiation can be formulated as given in Example VI. The substantive UV absorbers, both water-soluble ($\beta,\beta'$-di(p-methoxy cinnamidopropyldimethyl ammonium chloride)ethyl ether) and water-insoluble (compounds of Formula I) can be conveniently incorporated at 2.0% each w/w of total composition. To cover UV-A range butyl methoxy dibenzoyl methane (Parsol 1789) is incorporated.

Face powder compositions of the present invention contain compounds of Formula I in an effective amount of 0.1% w/w to 0.5% w/w.

The hair care and skin care compositions of the present invention containing compounds of Formula I and may contain one or more ingredients selected form cosmetic agents such as surfactants, other sunscreen chemicals, after sun treatment materials, emollients, humectants, perfumes, anti-perspirants, moisturisers, color cosmetic materials, herbal extracts, occlusive oils and essential oils.

The compositions of compound with Formula I provide hair protection from UV radiation in addition to good conditioning effect. The hair protecting preparations can be formulated in the form of creams, lotions, tonics or gels.

The compounds of the present invention may also be formulated as hair care product such as shampoos, cream rinses, hair conditioners, hair dressing preparations, hair relaxers, hair coloring products and the like, capable of protecting hair from UV-B radiation.

The rinse-off preparations like shampoos, face washes and bathing bars contain 0.5 to 10% w/w of compounds of Formula I. It may be noted that these quaternaries are compatible with usual anti-dandruff, anti-microbial agents like Zinc pyrithione, Irgasan, Pyroctone. Hence, these compounds of Formula I can be incorporated in anti-dandruff shampoos.

Despite their cationic nature, the compounds of Formula I are completely compatible with anionic surfactants like sodium lauryl ether sulphate. The water insolubility and cationic nature does not effect transparency of transparent shampoo. The shampoo formulation thus made has been shown to deposit the quaternary compounds on hair (Example III).

Soap bars, both opaque and transparent/translucent can be formulated with compounds of UV-absorbing and conditioning compounds of Formula I. In soap bars, the cinnamidoalkyl quaternary ammonium compounds can be incorporated from 0.5 to 10.0% w/w, more preferably from 1.0 to 2.0% w/w of total composition. It may be noted that the compounds of Formula I in the following combi-bar formulation are compatible with anionic surfactants.

Furthermore, the compounds of Formula I when incorporated into a typical detergent powder or other household cleaning product compositions based on phosphate, carbonate or zeolite builders, very effectively impart anti-fading effect to colored fabric because of their substantivity. Typical detergent and household cleaning product compositions in accordance with the present invention include one or more surfactants, selected from anionic, cationic, nonionic and amphoteric detergents, alone or in combination. A typical detergent powder has been shown to deposit cationic photofilters of the present invention on fabric (Example VII).

The hair and skin protecting and detergent and household cleaning compositions of the present invention are also formed by admixing, dissolving the compounds of Formula I with other ingredients as in respective conventional composition. The preferred cosmetic compositions are solutions, dispersions or emulsions. The compositions contain an effective amount of one or more of UV-absorbing and conditioning compounds of the present invention to prevent erythema and darkening of skin due to solar damage.

In general, an amount of compounds of Formula I of about 0.5% to about 10% w/w and preferably between 2.5 to 8.0% w/w in a cosmetic composition of compounds of Formula I is useful particularly in personal hair and skin care products, sunscreens and tanning lotions. Leave-on preparations like hair oil may contain 0.01% to 2.0% w/w of compounds of Formula I. Typically, the ingredients are combined with mixing and heating if necessary until a uniform, homogeneous product is formed. With respect to the emulsion products of the present invention, the water-soluble and water-insoluble ingredients are mixed separately and combined with suitable emulsifier, preferably a cationic emulsifier, to form an emulsion.

A sunscreen cream for everyday use can be formulated with both water-soluble UV-B absorber ($\beta,\beta'$-di(p-methoxy cinnamidopropyldimethyl ammonium chloride)ethyl ether, Indian Patent Appln. No. 903/Mum/2000) and water-insoluble UV-B absorbers (compounds of Formula I) and any effective UV-A absorber like Parsol-1789 with silicone conditioners and Vitamins meant for skin care.

Unlike the hydrophobic photofilters from the prior art that are PABA based, the organic-soluble quaternary ammonium compounds of the present invention are based on cinnamidoalkyl moiety and absorb very strongly in UV-B region (e.g. molar extinction coefficient, $\epsilon$ of p-methoxy cinnamidopropyldimethyllauryl ammonium tosylate was found to be 25,000 at $\lambda$max 310 nm). The cationic centre provides substantivity to skin, hair and fabric and the long alkyl chain provides the softening/conditioning effect.

The water insolubility and substantivity makes these molecules extremely attractive for external applications as against water-soluble molecules that may get absorbed through skin. In addition to these advantages, the compounds of the present invention are compatible with all commonly used cosmetic ingredients and are extremely stable. Despite being cationic surfactants, the compounds of the present invention are compatible with anionic surfactants and can be conveniently included in a transparent shampoo or a transparent bathing bar.

EXAMPLES

The invention will now be illustrated with the help of examples, Examples I and II for process of manufacture of compounds of Formula I and Examples III to VII for compositions. The examples are by way of illustrations only and in no way restrict the scope of invention. Many changes and modifications can be made within the scope of the present invention without departing from the spirit thereof and the invention includes all such modifications. A few formula variations for the preparation of shampoo, cream hair conditioner, transparent bathing bar, sunscreen cream and detergent powder with compounds of Formula I are illustrated in Examples III, IV, V, VI and VII respectively.

Example I
Process for Preparation p-methoxy Cinnamidopropyldimethyllauryl Ammonium Tosylate:

The compound of Formula I, wherein, $R_1$=—$OCH_3$; $R_2$=—H; $R_3,R_4$=$CH_3$; n=3; $R_5$=—$C_{12}H_{25}$; $R_7$=—$CH_3$ from ethyl-methoxy cinnamate.

Fatty alcohols were obtained from Henkel A. G. N,N-dimethylpropyldiamine and p-toluene sulphonyl chloride was obtained from BASF and Gayatri Chemicals respectively. Ethyl p-methoxy cinnamate was supplied by Galaxy Surfactants Ltd.

p-Methoxy cinnamidopropyldimethylamine was synthesised from ethyl p-methoxy cinnamate and N,N-dimethylpropyldiamine.

a) Preparation of p-methoxy Cinnamidopropyldimethylamine:

Ethyl p-methoxy cinnamate (206.0 g, 1.0 mole), N,N-dimethylpropyldiamine (306.0 g, 3.0 mole) and sodium methoxide (2.0 g) were charged in a pressure reactor. The air inside the reactor was flushed out by purging of nitrogen. The reaction mixture was then stirred at 180° C. (this generated pressure of 18 kg/cm$^2$) for 36 hours. The progress of reaction was monitored by disappearance of ethyl p-methoxy cinnamate on chromatography (TLC and HPLC). The TLC was performed on aluminium coated silica gel plates (Merck-60-F-254) and viewed with a UV lamp at 254 nm. HPLC was performed using reversed phase technique on a C-18 bonded (octadecyl silane) column and 60% aqueous methanol as mobile phase (1.0 ml/min) and detection at 280 nm. The excess amine was removed under vacuum. The golden yellow solid (263.0 g) thus obtained had amine value of 245. Molar extinction coefficient, $\epsilon$, in methanol was found to be 24,224 at 290 nm.

IR in dichloromethane showed carbonyl stretching of amide at 1660 cm$^{-1}$ and NH stretching at 3300 cm$^{-1}$. $^1$H NMR (300 MHz, CDCl$_3$): $\delta$1.73 (p, 2H, J=6.6 Hz), 2.26 (s, 6H), 2.42 (t, 2H, J=6.6 Hz), 3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J =8.7 Hz), 7.53 (d, 1H, J =15.6 Hz).

b) Preparation of Lauryl Tosylate:

To a stirred and a cooled solution of lauryl alcohol (186.0 g, 1.0 mole) and triethyl amine (121.0 g, 1.2 mole) in dichloromethane (600 ml), p-toluene sulphonyl chloride (228.0 g, 1.2 mole) in dichloromethane (400 ml) was slowly added and the reaction was continued at room temperature for 10 hours. The reaction mixture was then washed with 20% sodium chloride solution (500 ml). The washed organic layer was dried over anhydrous sodium sulphate. Removal of solvent under vacuo resulted in colorless oil that solidified on keeping to yield lauryl tosylate. (309.0 g, 91%), m. p. 29° C. (literature m. p. 29° C.).

c) Preparation of p-methoxy Cinnamidopropyldimethyllauryl Ammonium Tosylate:

A mixture of lauryl tosylate (306.0 g, 0.9 mole) and p-methoxy cinnamidopropyldimethyl amine (235.8 g, 0.9 mole) was stirred under blanket of nitrogen at 110° C. for 20 hours. The progress of reaction was monitored by estimation of unquaternised amine. On cooling, the reaction yielded pale yellow solid that was crystallised from isopropanol to give quaternary ammonium compound as white solid (501.0 g) with m. p. 130–135° C.

IR (CH$_2$Cl$_2$): 1656 cm$^{-1}$ carbonyl of amide.
$^1$H NMR (CDCl$_3$, 300 MHz): $\delta$0.87 (3H, t, J=6.3 Hz), 1.18 (18H, broad signal), 1.58 (2H, unresolved multiplet), 2.10 (2H, unresolved multiplet), 2.32 (3H, singlet, methyl of tosyl), 3.13 (6H, singlet, two methyl on nitrogen), 3.20 (2H, unresolved multiplet), 3.45 (2H, unresolved multiplet), 3.68 (2H, unresolved multiplet), 3.78 (3H, singlet, OCH$_3$), 6.52 (1H, d, J=15.6 Hz), 6.76 (2H, d, J=8.4 Hz), 7.14 (2H, d, J =6.0 Hz), 7.31 (2H, d, J=8.6 Hz), 7.48 (1H, d, J=15.6 Hz), 7.78 (2H, d, J=7.8 Hz).

The molar extinction coefficient, $\epsilon$ was found to be 25,000 at $\lambda$max 310 nm in methanol.

The final compound was analysed on HPLC using ion-pairing technique. The mobile phase employed for ion-pairing comprised of 0.1 M octane sulphonic acid in aqueous methanol (70:30). Reversed phase column Chromspher C8 was used with mobile phase flow rate of 1.0 ml/min. The detection was done at 280 nm. The retention time for p-methoxy cinnamidopropyldimethyllaurylamine was found to be 10.0 minutes.

The purity of final compound from this analysis was found to be 98.0% with 2.0% unquaternised amine.

Example II
Process for Preparation p-methoxy Cinnamidopropyldimethyllauryl Ammonium Tosylate:

The compound of Formula I, wherein, $R_1$=—$OCH_3$; $R_2$=—H; $R_3,R_4$=$CH_3$; n=3; $R_5$=—$C_{12}H_{25}$; $R_7$=—$CH_3$ from-methoxy cinnamoyl chloride. p-Methoxy cinnamidopropyldimethylamine was synthesised from p-methoxy cinnamoyl chloride and N,N-dimethylpropyldiamine.

(a) Preparation of p-methoxy Cinnamoyl Chloride:

To a stirred suspension of p-methoxy cinnamic acid (178.0 g, 1.0 mole) in dichloromethane (500 ml), thionyl chloride (238.0 g, 2.0 moles) was added slowly and the reaction mass was heated at 45° C. for 3 hours. The excess of thionyl chloride was removed under vacuum and the-methoxy cinnamoyl chloride was distilled (145° C./0.2 mm) in 85% yield as colourless solid with m. p. 50° C. (Literature m.p. 50° C., Dictionary of Organic Compounds, Chapmann and Hall, 1994).

(b) Preparation of p-methoxy Cinnamidopropyldimethylamine:

To a stirred solution of N,N-dimethylpropyldiamine (102.0 g, 1.0 mole) in dichloromethane (500 ml), solution of p-methoxy cinnamoyl chloride (196.0 g, 1.0 mole) in dichloromethane from step (a) was slowly added and the reaction was continued at room temperature for 2 hours. The reaction mixture in dichloromethane was washed with aqueous sodium hydroxide (200 ml, 20.0%). The organic layer was dried over anhydrous sodium sulphate. The removal of solvent using a rotary evaporator afforded the p-methoxy cinnamidopropyldimethylamine (235.0 g) as colourless solid, m.p. 80° C. Reversed phase HPLC showed it to be 98% pure with amine value 217.

The NMR, IR and HPLC data matched with the data for the compound obtained in Example I.

(c) Preparation of Lauryl Tosylate

Lauryl tosylate was synthesised as per step (b) of Example I.

(d) Preparation of p-methoxy Cinnamidopropyldimethyllauryl Ammonium Tosylate:

A mixture of lauryl tosylate (153.0 g, 0.45 mole), p-methoxy cinnamidopropyldimethyl amine (118.0 g, 0.45 mole) and isopropanol (270 ml) was refluxed under blanket of nitrogen at 85° C. for 48 hours. Isopropanol was removed on a rotary evaporator using temperature and vacuum. The NMR, melting point of solid quaternary ammonium compound thus obtained matched with that of Example I.

The purity of final compound from this analysis was found to be 97.2% with 1.8% unquaternised amine by ion pairing HPLC.

Example III
Preparation of Transparent Shampoo

A transparent shampoo was formulated using p-methoxy cinnamidopropyldimethyllauryl ammonium tosylate prepared as in Example I. The other active ingredients, SLES-2, Sodium lauryl ether sulphate, an anionic surfactant, 30% aqueous solution, CAPB, Cocoamidopropyl betaine, an amphoteric surfactant, 30% aqueous solution and Galsilk, Polyquaternium-7 were obtained from Galaxy Surfactants Ltd., Mumbai, India. Methyl paraben and propyl paraben were obtained from Gayatri Laboratories, Mumbai, India. Approved fragrances and colors were obtained from S. H. Kelkar & Co., Mumbai, India and Koel Colors Pvt. Ltd., Mumbai, India respectively.

A shampoo composition containing p-methoxy cinnamidopropyldimethyllauryl ammonium tosylate of Example I was prepared in accordance with the optimum formulation given below. Acceptable formula variations for the preparation of such shampoo are also illustrated.

| Ingredient | Range % (w/w) | Preferred % (w/w) | Optimum % (w/w) |
| --- | --- | --- | --- |
| SLES-2 (30%) | 40–60 | 45–60 | 50.00 |
| CAPB (30%) | 1–10 | 2–10 | 8.00 |
| p-methoxy cinnamidopropyl dimethyllauryl ammonium tosylate | 0.5–10 | 2–5 | 2.00 |
| Galsilk | 3–10 | 4–6 | 5.00 |
| Sodium chloride | | Quantity sufficient | |
| Preservatives/colour and fragrance/ chelating agents | | Quantity sufficient | |
| Deionised water | | Quantity sufficient to make 100% | |

The Transparent Shampoo was Prepared as Follows:

The ingredients were mixed with heating to 50° C. until a uniform homogenous mixture was formed. The resulting mixture was then cooled to room temperature with continuous stirring. The required chelating agent, colour, perfume were added. The viscosity was adjusted to 2500 cps with sodium chloride.

The p-methoxy cinnamidopropyldimethyllauryl ammonium tosylate was found to be completely compatible with anionic surfactant. The substantivity experiment was performed as described under;

Virgin hair (5.0 g) were washed with 10% SLES solution and rinsed with plain water. The tresses were treated for exactly 5.0 minutes with clear shampoo (containing 2% p-methoxy cinnamidopropyldimethyllauryl ammonium tosylate) as described in Example I that was diluted five times with water. After the treatment the tresses were washed thoroughly with copious amount of water. The adsorbed quaternary was extracted from the hair surface by immersing each tress in isopropanol at 65° C. for 30 minutes. A known volume of this isopropanol/quaternary ammonium salt mixture was analysed by UV-spectroscopy to determine its absorption intensity.

The substantivity was found to be 37 mg/100 g of hair.

Example IV
Preparation of cream hair conditioner

Cetyltrimethylammonium chloride was obtained from Flame Pharmaceuticals Pvt. Ltd., Mumbai, India, Isopropyl myristate was obtained from Anusynth Chemical Industries, Mumbai, India, Lanoline was obtained from Rolex Lanoline Products Ltd., Mumbai, India. Phenoxyethanol and β,β'-di (p-methoxy cinnamidopropyldimethyl ammonium chloride) ethyl ether (a water-soluble cationic UV-B sunscreen, Indian Patent Appln. No. 903/Mum/2000) were obtained from Galaxy Surfactants Ltd., Mumbai, India.

A cream hair conditioner containing p-methoxy cinnamidopropyldimethyllauryl ammonium tosylate of Example I was prepared in accordance with the optimum formulation given below. Acceptable formula variations for the preparation of such cream hair conditioner are also illustrated.

| Ingredient | Range % (w/w) | Preferred % (w/w) | Optimum % (w/w) |
| --- | --- | --- | --- |
| p-methoxy cinnamidopropyl dimethyllauryl ammonium tosylate | 0.5–5 | 1–3 | 2.0 |
| β,β'-di(p-methoxy cinnamidopropyl dimethyl ammonium chloride)ethyl ether | 0.5–5 | 1–3 | 2.0 |
| Cocoamidopropyl betaine | 1–6 | 0.5–2 | 0.5 |
| Cetyl trimethyl ammonium chloride | 1–15 | 4–10 | 4.5 |
| Cetostearyl alcohol | 1–15 | 5–10 | 5.5 |
| Lanoline | 0.5–10 | 1–5 | 1.5 |
| Isopropyl myristate | 0.5–5 | 1–3 | 1.0 |
| Chelating agents/preservatives/ fragrances | | Quantity sufficient | |
| Deionised water | | Quantity sufficient to make 100% | |

The cream hair conditioner was prepared as follows:

Aqueous phase containing cetyltrimethylammonium chloride, cocoamidopropyl betaine, β,β'-di(p-methoxy cinnamidopropyldimethyl ammonium chloride)ethyl ether and water were stirred together at 70° C. Oily phase comprising cetostearyl alcohol, isopropyl myristate, lanoline, p-methoxy cinnamidopropyldimethyllauryl ammonium tosylate and preservatives was maintained at 70° C. under stirring. The oily phase is slowly added to the stirred aqueous phase at 70° C. and the whole mixture was cooled under vigorous stirring to 40° C. Perfume and other additives were added and continued cooling under stirring to get good cream.

Example V
Preparation of Transparent Bathing Bar

A transparent bathing bar containing p-methoxy cinnamidopropyldimethyllauryl ammonium tosylate of Example I was prepared in accordance with the optimum formulation given below. Acceptable formula variations for the preparation of such transparent bathing bar are also illustrated.

| Ingredient | Range % (w/w) | Preferred % (w/w) | Optimum % (w/w) |
|---|---|---|---|
| SLES (30%) | 10–50 | 20–35 | 28 |
| CAPB (30%) | 5–30 | 10–20 | 16 |
| Sodium cocoate | 5–20 | 10–15 | 9.0 |
| Sodium stearate | 15–70 | 15–20 | 13.8 |
| Propylene Glycol | 10–30 | 10–25 | 20 |
| Sorbitol (70%) | 4–15 | 8–10 | 8.0 |
| p-methoxy cinnamidopropyl dimethyllauryl ammonium tosylate | 0.5–10 | 1.0–5.0 | 2.0 |
| Chelating agent/colour and fragrance/ | Quantity sufficient | | |
| Deionised water | Quantity sufficient to make 100% | | |

The transparent bathing bar was prepared as follows:

All ingredients were heated together under stirring to 70° C. till the reaction mass became homogenous and transparent. The reaction mass was cooled to 40° C. and the required amounts of perfume and colour were added. The molten mass was cast in moulds of desired shape to yield transparent bathing bar. It could be easily seen that the transparency of bathing bar was unaffected proving the total compatibility of p-methoxy cinnamidopropyldimethyllauryl ammonium tosylate with anionic surfactant. The transparent bar thus made was evaluated as per the procedure described in Example III and the substantivity was found to be 29 mg/100 g of hair.

Example VI
Preparation of Sunscreen Cream

Parsol—1789 was procured from Givaudan, Roure, USA. Tween-80, Niacinamide and Vitamin E acetate were obtained from S. D. Fine Chem., Mumbai, India. Lauryl alcohol ethoxylate, ethylene glycol monostearate, glyceryl monostearate were obtained from Galaxy Surfactants Ltd., Mumbai, India. Dimethicone copolyol (SF 1188A) was obtained from General Electric, Bangalore, India.

A sunscreen cream for every day use containing p-methoxy cinnamidopropyldimethyllauryl ammnonium tosylate of Example I was prepared in accordance with the optimum formulation given below. Acceptable formula variations for the preparation of such sunscreen cream are also illustrated.

| Ingredient | Range % (w/w) | Preferred % (w/w) | Optimum % (w/w) |
|---|---|---|---|
| p-methoxy cinnamidopropyl dimethyl-lauryl ammononium tosylate | 1–10 | 1–5 | 2.0 |
| β,β'-di(p-methoxy cinnamidopropyl-dimethyl ammononium chloride)ethyl ether | 1–10 | 1–5 | 1.0 |
| Parsol-1789 (UV-A filter) | 1–5 | 1–3 | 1.0 |
| Polysorbate-80 (Tween-80) | 1–12 | 3–7 | 5.0 |
| Lauryl alcohol ethoxylate - 9 EO | 1–12 | 3–7 | 5.0 |
| Liquid paraffin oil | 1–12 | 3–7 | 5.0 |
| Isopropyl myristate | 1–12 | 3–7 | 5.0 |
| Ethylene glycol monostearate | 1–12 | 3–7 | 5.0 |
| Glyceryl monostearate | 1–12 | 3–7 | 5.0 |
| Cetostearyl alcohol | 1–12 | 3–7 | 5.0 |
| Dimethicone copolyol | 1–10 | 2–3 | 2.0 |
| Vitamin E acetate | 0.5–5 | 1–3 | 0.5 |
| Niacinamide | 0.5–5 | 1–3 | 1.0 |
| Hydroquinone | 0.5–3 | 1–2 | 1.0 |
| Sodium sulphite | 0.1–1 | 0.1–0.5 | 0.2 |
| Preservatives/fragrance | Quantity sufficient | | |
| Deionised water | Quantity sufficient to make 100% | | |

The Sunscreen Cream was Prepared as Follows:

Aqueous phase containing β,β'-di(p-methoxy cinnamidopropyldimethyl ammonium chloride)ethyl ether, Tween-80, lauryl alcohol ethoxylate—9 EO, sodium sulphite, dimethicone copolyol and water was stirred at 70° C. The oily phase comprising of p-methoxy cinnamidopropyl dimethyl-lauryl ammonium tosylate, isopropyl myristate, paraffin oil, glyceryl monostearate, ethylene glycol monostearate, Vitamin E acetate, cetostearyl alcohol, niacinamide, hydroquinone and the preservatives was heated under stirring to 70° C. The oily phase is then added to the vigorously stirred aqueous phase and cooled under stirring to 40° C. At this stage fragrances were added and cooled under stirring to room temperature to get a good shiny cream.

Example VII
Preparation of Detergent Powder

Linear alkyl benzene sulphonic acid was obtained from Albright and Wilson Chemicals (India) Ltd., Mumbai, India.

A detergent powder containing p-methoxy cinnamidopropyldimethyllauryl ammonium tosylate of Example II was prepared in accordance with the optimum formulation given below. Acceptable formula variations for the preparation of such detergent powder are also illustrated.

| Ingredient | Range % (w/w) | Preferred % (w/w) | Optimum % (w/w) |
|---|---|---|---|
| Soda ash | 20–50 | 20–30 | 20 |
| Sodium tripolyphosphate | 1–30 | 15–25 | 25 |
| Sodium alkyl benzene sulphonate | 10–50 | 10–30 | 20 |
| Sodium chloride | 1–45 | 5–15 | 5.0 |
| Sodium sulphate | 1–40 | 10–20 | 20 |
| p-methoxy cinnamidopropyl dimethyllauryl ammonium tosylate | 0.5–10 | 2–4 | 4.0 |
| Sodium carboxy methyl cellulose | 0.5–5 | 1–2 | 1.0 |
| Sodium silicate | 1–5 | 1–2 | 2.0 |
| Chelating agent/colour and fragrance | Quantity sufficient | | |

The Detergent Powder was Prepared as Follows:

To a stirred mixture of soda ash, sodium tripolyphosphate, sodium chloride and sodium sulphate, linear alkyl benzene sulphonic acid was slowly added. The mixture was then cooled to room temperature. Other active ingredients including sodium carboxy methyl cellulose, sodium silicate and p-methoxy cinnamidopropyldimethyllauryl ammonium tosylate were then added to this mixture along with the other additives like nonionic surfactant, bleaching agent, optical brightener, chelating agent, colour and perfume and stirring was continued to get uniform detergent powder.

The detergent thus made was evaluated for the deposition of quaternary on cotton fabric (substantivity) as per the principles described in Example III and was found to be 27 mg/100 g of cotton fabric.

What is claimed is:

1. A quaternary armnonium salt of cinnamidoalkylamine of Formula I,

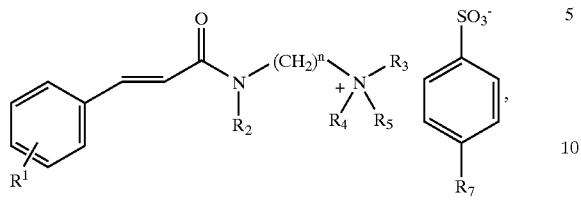

wherein $R_1$ is a substituent selected from H, halo, OH, $-NH_2$, $-NO_2$, $-OCH_3$, $-N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from alkyl groups containing from 1 to 12 carbon atoms;

$R_3$ and $R_4$ are independently selected from benzyl or alkyl groups containing from 1 to 12 carbon atoms, n is an integer from 1 to 6;

$R_5$ is selected from an alkyl group containing from 8 to 22 carbon atoms or alkenyl groups containing from 8 to 22 carbon atoms; and $R_7$ is selected from bromo, chloro, nitro, methyl and ethyl groups.

2. A quaternary salt of claim 1, wherein the compound of formula I is p-methoxy cinnamidopropyldimethyllauryl ammonium tosylate, wherein, $R_1$=para $-OCH_3$, $R_3$=$-CH_3$, $R_5$=$-C_{12}H_{25}$, n=3 and the counter anion=tosylate anion.

3. A process of making a quaternary ammonium salt of cinnamidoalkylamine of Formula I,

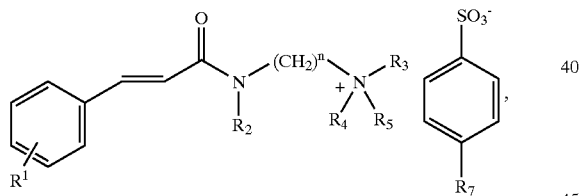

wherein $R_1$ is a substituent selected from H, halo, OH, $-NH_2$, $-NO_2$, $-OCH_3$, $-N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from hydrogen or alkyl groups containing from 1 to 12 carbon atoms;

$R_3$ and $R_4$ are independently selected from benzyl or alkyl groups containing from 1 to 12 carbon atoms, n is an integer from 1 to 6;

$R_5$ is selected from an alkyl group containing from 8 to 22 carbon atoms or alkenyl groups containing from 8 to 22 carbon atoms; and $R_7$ is selected from bromo, chloro, nitro, methyl and ethyl groups, wherein a compound of Formula II is reacted with a compound of Formula III to give an intermediate of Formula TV, the intermediate of formula IV is quaternised with a compound of Formula V, wherein $R_1$, $R_2$, $R_3$, $R_4$, $R_5$, $R_7$, n are the same as in Formula I and $R_6$ of Formula II is selected from $-OH$, CL or $-O(CH_2)_p CH_3$ with p=0 to 3 to provide the compound of formula I

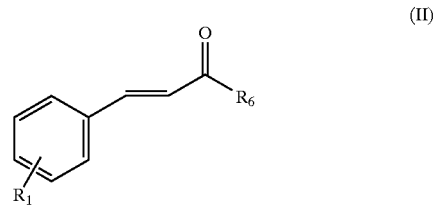

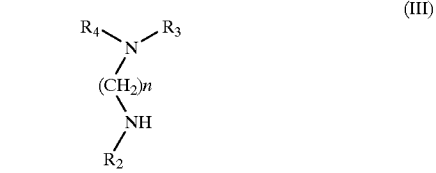

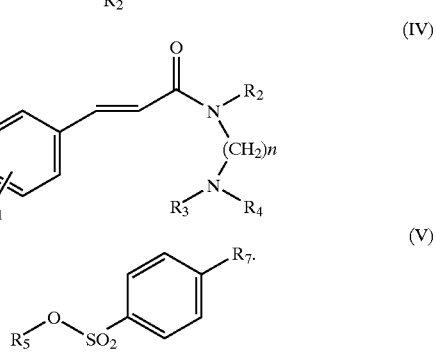

4. A composition comprising a cinnamidoalkylamine cationic salt of claim 1 and one or more other ingredients selected from the group consisting of aqueous and oily moisturizers, film forming agents, emulsifiers, thickening agents, skin and hair conditioning agents, vegetable oils, humectants, surfactants, detergents, emollients and rheological modifiers.

5. A composition comprising from 0.01% to 10% w/w of a quaternary ammonium salt of cinnamidoalkylamine Formula I and one or more other ingredients, wherein said Formula I is

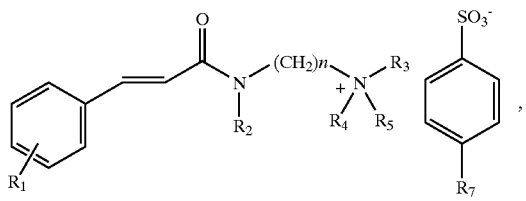

wherein $R_1$ is a substituent selected from H, halo, OH, $-NH_2$, $-NO_2$, $-OCH_3$, $-N(CH_3)_2$, alkyl groups containing from 1 to 6 carbon atoms, alkoxy groups containing from 1 to 6 carbon atoms, alkylamino or N,N-dialkylamino groups containing from 1 to 6 carbon atoms;

$R_2$ is selected from alkyl groups containing from 1 to 12 carbon atoms;

$R_3$ and $R_4$ are independently selected from benzyl or alkyl groups containing from 1 to 12 carbon atoms, n is an integer from 1 to 6;

$R_5$ is selected from an alkyl group containing from 8 to 22 carbon atoms or alkenyl groups containing from 5 to 22 carbon atoms; and R$_7$ is selected from bromo, chloro, nitro, methyl and ethyl groups, wherein said one or more other ingredients are present in an amount of about 25% w/w of the composition, and are selected from the group consisting of aqueous and oily moisturizers, film forming agents, emulsifiers, thickening agents, skin and hair conditioning agents, vegetable oils, humectants, surf actants, detergents, emollients and rheological modifiers, and wherein said detergents are selected from the group consisting of anionic detergents, cationic detergents, non-ionic detergents and amphoteric detergents.

6. The composition of claim 4, wherein the other ingredients are present in an amount of about 25% w/w of said composition.

7. The composition of claim 4, wherein said cinnamidoalkylamine quaternary salt is present in an amount in the range from about 0.01% to about 10.0% w/w of said composition.

8. The composition of claim 4, wherein the other ingredients are chosen to give a shampoo formulation.

9. The composition of claim 4, wherein the other ingredients are chosen to give a hair conditioner formulation.

10. The composition of claim 5, wherein the other ingredients are chosen to give a bathing bar formulation.

11. The composition of claim 5, wherein the other ingredients are chosen to give a sunscreen cream formulation.

12. The composition of claim 5, wherein the other ingredients are chosen to give a detergent powder formulation.

13. A quaternary ammonium salt of cinnamidoalkylamine of Formula I according to claim 1, wherein said R$_1$ is a substituent selected from H, halo, OH, —NH$_2$, —NO$_2$, —OCH$_3$, —N(CH$_3$)$_2$, alkyl groups containing from 1 to 6 carbon atoms, alkoxy groups containing from 1 to 6 carbon atoms, alkylamino or N,N-dialkylamino groups containing from 1 to 6 carbon atoms;

R$_2$ is selected from alkyl groups containing from 1 to 12 carbon atoms;

R$_3$ and R$_4$ are independently selected from benzyl or alkyl groups containing from 1 to 12 carbon atoms;

n is an integer from 1 to 6;

R$_5$ is selected from alkyl groups containing from 8 to 22 carbon atoms or alkenyl groups containing from 8 to 22 carbon atoms;

R$_7$ is selected from bromo, chloro, nitro, methyl and ethyl groups.

14. A process according to claim 3, wherein

R$_2$ is selected from alkyl groups containing from 1 to 12 carbon atoms.

15. The composition of claim 5, wherein the other ingredients are chosen to give a shampoo formulation.

16. The composition of claim 5, wherein the other ingredients are chosen to give a hair conditioner formula.

* * * * *